(12) United States Patent
Lali et al.

(10) Patent No.: US 10,465,257 B2
(45) Date of Patent: Nov. 5, 2019

(54) PROCESS FOR PRODUCTION OF PURE GLUCOSE FROM CELLULOSE

(71) Applicants: Institute of Chemical Technology, Mumbai (IN); The Coca-Cola Company, Atlanta, GA (US)

(72) Inventors: Arvind Mallinath Lali, Mumbai (IN); Annamma Anil Odaneth, Mumbai (IN); Juliet Joanna Victoria, Mumbai (IN); Vikram Gunvant Choudhari, Mumbai (IN); Prathamesh Chandrashekhar Wadekar, Mumbai (IN); Mallikarjun Laxmiputra Patil, Mumbai (IN); Parmeshwar Shivajirao Patil, Mumbai (IN); Bhupal Ravindra Asodekar, Mumbai (IN); Chinmayee Ramray Mahadik, Mumbai (IN); Indra Prakash, Alpharetta, GA (US); Xiaoyan Huang, Atlanta, GA (US)

(73) Assignees: Institute of Chemical Technology, Mumbai, Maharashtra (IN); The Coca-Cola Company, Atlanta, GA (US)

( * ) Notice: Subject to any disclaimer, the term of this patent is extended or adjusted under 35 U.S.C. 154(b) by 91 days.

(21) Appl. No.: 15/746,217

(22) PCT Filed: Jul. 22, 2016

(86) PCT No.: PCT/IN2016/050248
§ 371 (c)(1),
(2) Date: Jan. 19, 2018

(87) PCT Pub. No.: WO2017/013684
PCT Pub. Date: Jan. 26, 2017

(65) Prior Publication Data
US 2018/0209002 A1 Jul. 26, 2018

(30) Foreign Application Priority Data

Jul. 22, 2015 (IN) .......................... 2782/MUM/2015

(51) Int. Cl.
| | |
|---|---|
| C13K 1/04 | (2006.01) |
| C12P 19/14 | (2006.01) |
| C12P 19/24 | (2006.01) |
| A23L 29/30 | (2016.01) |
| A23L 33/125 | (2016.01) |
| A23L 2/60 | (2006.01) |
| C12P 19/02 | (2006.01) |
| C13K 11/00 | (2006.01) |

(52) U.S. Cl.
CPC .................. *C13K 1/04* (2013.01); *A23L 2/60* (2013.01); *A23L 29/30* (2016.08); *A23L 33/125* (2016.08); *C12P 19/02* (2013.01); *C12P 19/14* (2013.01); *C12P 19/24* (2013.01); *C12Y 302/01004* (2013.01); *C12Y 503/01018* (2013.01); *C13K 11/00* (2013.01); *A23V 2002/00* (2013.01); *C12P 2201/00* (2013.01); *C12P 2203/00* (2013.01)

(58) Field of Classification Search
None
See application file for complete search history.

(56) References Cited

U.S. PATENT DOCUMENTS

| | | | |
|---|---|---|---|
| 4,017,363 A | 4/1977 | McMullen et al. | |
| 4,025,389 A | 5/1977 | Poulsen et al. | |

FOREIGN PATENT DOCUMENTS

EP 2336343 A1 6/2011

OTHER PUBLICATIONS

Dussan et al, dilute acid hydrolysis of cellulose to glucose from sugarcane biomass, chemical engineering transactions, pp. 433-437 (Year: 2014).*
Monavari et al., "The influence of solid/liquid separation techniques on the sugar yield in two-step dilute acid hydrolysis of softwood followed by enzymatic hydrolysis." Biotech. for Biofuels, 2009, 2(6):1-9.
Alriksson et al., "Optimal conditions for alkaline detoxification of dilute-acid lignocellulose hydrolysates." App. Biochem. Biotech., 2006, 129-132(1-3): 599-611.
Hong et al., "Fractionation and delignification of empty fruit bunches with low reaction severity for high sugar recovery." Bioresource Tech., 2012, 146: 176-183.

(Continued)

*Primary Examiner* — Melvin C. Mayes
*Assistant Examiner* — Stefanie J Cohen
(74) *Attorney, Agent, or Firm* — Thomas|Horstemeyer, LLP

(57) ABSTRACT

The present disclosure provides a process for production of glucose having purity greater than 98% from pretreated cellulosic biomass comprising 50-95% cellulose, using thermo-chemical and enzymatic treatments. The process of the disclosure involves mild acid and/or alkali treatment of the pretreated cellulosic biomass for production of treated cellulosic biomass residue comprising polysaccharides containing greater than 98% glucose. The treatment results in high purity cellulose that is highly amenable to enzymatic hydrolysis and yields glucose having purity greater than 98%. The process of the disclosure also involves membrane separation of enzymes and oligosaccharides for recycling and separation of glucose to avoid product feedback inhibition.

21 Claims, No Drawings

(56) References Cited

OTHER PUBLICATIONS

Lenihan et al., "Dilute acid hydrolysis of lignocellulosic biomass." Chem. Engr., 2010, 156(2):395-403.
Kim et al., "Sequential acid-/alkali-pretreatment of empty palm fruit bunch fiber." Bioresource Tech., 2012, 109: 229-233.
International Search Report for PCT/IN2016/050248 dated Dec. 15, 2016.

* cited by examiner

PROCESS FOR PRODUCTION OF PURE GLUCOSE FROM CELLULOSE

FIELD OF INVENTION

The present disclosure relates to a process for production of glucose having purity greater than 98% from a pretreated cellulosic biomass. Furthermore, it relates to obtaining a treated cellulosic biomass residue comprising polysaccharides that contain greater than 98% glucose units, which is amenable to enzymatic treatment for production of greater than 98% glucose purity.

BACKGROUND OF THE INVENTION

World's increasing demand for energy and food can be met by use of non-edible agricultural produce like lignocellulosic biomass. Lignocellulosic biomass, e.g. as obtained from agricultural farm and industry residues, has proven to be a potential and sustainable resource as feedstock for production of sugars that are precursors for fuels, chemicals, feed and food products e.g. cellulosic ethanol, organic acids like lactic acid and succinic acid, cellulose, and food additives like xylitol.

Agricultural residues that can be used include rice straw, wheat straw, corn cob, corn stover, sugarcane bagasse, stevia leaves etc., while on the other hand lignocellulosic feedstocks may also be derived from forest products as well as by-products of agricultural industry. Commonly referred to as lignocellulosic biomass, or simply cellulosic biomass, the biomass constitutes an intricate complex of cellulose, hemicelluloses and lignin. Conversion of these substrates into sugars and further products involves three major steps; pretreatment, hydrolysis followed by chemical or biochemical transformation.

The pretreatment of the substrates can be designed so that it fractionates the substrate biomass into lignin and holocellulose (a mixture of cellulose and hemicellulose). While lignin can be used for the production of value added chemicals, the holocellulose components obtained can be hydrolysed using a combination of enzymes called cellulases for release of sugars. These sugars find uses for production of chemicals and materials through one or more combinations of chemical and biological transformations. The sugars, in addition to being precursors to fuels, energy and chemicals, can also find uses in food and pharmaceutical industry if isolated and purified to required levels.

Pretreatment is aimed at loosening the bonds between cellulose, hemicellulose and lignin. Acid pretreatment is the most widely used method but suffers from being non-ecofriendly and requires expensive material of construction besides giving lower yields of mono-sugars and forming fermentation toxic side products. Hydrothermal or steam explosion is the next popular choice but suffers from scalability problems. Alkali hydrolysis is expensive but produces high quality cellulosic residues and gives higher yields of fermentable sugars. Other options like AFEX, and solvent processes are not likely to find acceptance on account of the costs involved.

The choice of a method is decided by many factors, the most important being the type of biomass. Biomass is graded on the basis of severity of pre-treatment required to obtain enzyme hydrolysable biomass. Thus, while bagasse is a 'low-severity' biomass, wood-chips and cotton or jatropha plant waste are 'high-severity' biomass. Most agricultural grain residues would classify as low to medium severity biomass.

Most pre-treatment technologies leave residual solid mass that is 'de-lignified' and 'softened' for hydrolysis to sugars.

Option lies between sending the whole biomass through the next saccharification step without fractionation into separated components or sending the biomass into saccharification after separation of the fractionated components namely cellulose, hemicellulose and lignin. The earlier approach is normally preferred when all combined sugars i.e. glucose, xylose and others are to be together converted to ethanol. However, delignification is an important step as the products of lignin degradation e.g. phenolics, acetic acid, formic acid etc. are known to be inhibitory to the subsequent conversion processes.

Over the period of time, it has become apparent that separation of biomass into its constituent components namely, cellulose, hemicellulose and lignin has several advantages. These advantages include higher yields of sugars and lower consumption of enzyme in the saccharification step, especially when the objective is to make high purity sugars. Saccharification step constitutes the hydrolysis reactions whereby the polymeric cellulose and hemicellulose are broken down to their monomeric components. While many non-biological routes have been tried, it is by and large established that enzymatic hydrolysis can best provide sugars in high yields with lower formation of undesirable by-products.

There are, however, a number of issues that need attention in order to use the enzyme hydrolysis technology for commercial or scalable applications. The hydrolysis or enzymatic saccharification involves use of cellulases; most often a mixture of one or more each of endoglucanases, exoglucanases and glucosidases for breaking of cellulose polysaccharides into monomeric glucose moieties. It is a well documented fact that during the course of hydrolysis as glucose begins to accumulate in the system, glucosidase enzyme is inhibited leading to cellobiose accumulation. This causes inhibition of exoglucanases and endoglucanases with the overall result that the saccharification process stalls short of 100%. The result is a mixture of sugars consisting of monosaccharides like glucose, xylose, arabinose; disaccharide and oligosaccharides like cellobiose and cello-oligosaccharide, respectively.

Oligosaccharide and disaccharide concentrations differ depending on the reaction conditions and may vary from 0.1 mg/ml in low substrate loading reactions to 50 mg/ml where the substrate concentration is as high as 20%. Hydrolysis or separation of these oligosaccharides to monosaccharide is a prerequisite if high purity food grade glucose (more than 99.5% pure) is the desired product or even when the final product is used for conversions of glucose to other value added products.

There are several factors of concern in the economics of production of sugars by known methods for conversion of a cellulosic biomass to glucose. Since the demand of cellulose derived high purity glucose is likely to find increasing applications and acceptance in food industry and many other industries, a robust method capable of providing homogeneous and high purity glucose is therefore necessary.

SUMMARY OF THE INVENTION

In an aspect of the present disclosure, there is provided a process for production of glucose having purity of greater than 98% from pre-treated cellulosic biomass comprising the steps of: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate, and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, and cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

In an aspect of the present disclosure, there is provided glucose produced by a method comprising the steps of: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate, and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, and cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

In an aspect of the present disclosure, there is provided fructose prepared from glucose using glucose isomerase, said glucose is produced by a method comprising the steps of: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate, and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, and cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

In an aspect of the present disclosure, there is provided a mixture of glucose and fructose, wherein glucose is obtained by a method comprising the steps of: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate, and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, cellotriose, and combinations thereof (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity; and is converted to fructose using glucose isomerase.

In an aspect of the present disclosure, there is provided a consumable product comprising glucose, fructose, or a mixture of glucose and fructose, wherein glucose is prepared by a method comprising the steps: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate, and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity; fructose is prepared from glucose using glucose isomerase; and the product is selected from the group consisting of a food, a beverage, a pharmaceutical composition, a tobacco product, a nutraceutical composition, an oral hygiene composition, and a cosmetic composition.

In an aspect of the present disclosure, there is provided a process for production of glucose having purity of greater than 98% from pre-treated cellulosic biomass comprising the steps of: (a) subjecting a pre-treated cellulosic biomass comprising 60% to 90% cellulose to a two-step acid-acid treatment method to obtain a treated cellulosic biomass residue comprising 98-99% cellulose, wherein said acid-acid treatment comprises: (i) contacting pre-treated cellulosic biomass with acid having concentration in the range of 1-3% (w/w) at a temperature in the range of 100° C.-130° C. for period of 5 minutes to 20 minutes to obtain a first cellulosic biomass comprising cellulose having concentration in the range of 80-95% and (ii) contacting said first cellulosic biomass with acid having concentration in the range of 1-3% (w/w) at a temperature in the range of 100° C.-130° C. for period of 5 minutes to 20 minutes to obtain a treated cellulosic biomass residue comprising cellulose having concentration in the range of 98-99%; (b) contacting said treated cellulosic biomass residue with cellulase at a concentration in the range of 40-50 mg/g of treated cellulosic biomass residue at a temperature in the range of 40° C.-50° C. for period of 90 minutes to 120 minutes to obtain cellulose hydrolysate, and insoluble components, wherein said cellulose hydrolysate comprises sugars containing 90 to 98% of monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise more than 99% glucose, and a retentate fraction comprising oligomers, cellobiose, cellotriose, and combinations thereof; (e) treating the retentate fraction with β-glucosidase to obtain a sugar solution wherein the said sugar comprises greater than 99% glucose purity, and separating the sugar solution from β-glucosidase; and (f) mixing the permeate fraction and sugar solution to obtain greater than 98% glucose purity.

In an aspect of the present disclosure, there is provided a process for production of glucose having purity of greater than 98% from pre-treated cellulosic biomass comprising the steps of: (a) subjecting pre-treated cellulosic biomass comprising 60% to 90% cellulose to a three-step acid-alkali-acid treatment method to obtain a treated cellulosic biomass residue comprising 98-99% cellulose, wherein said acid-alkali-acid treatment comprises: (i) contacting pre-treated cellulosic biomass with acid having concentration of in the range of 1-3% (w/w) at a temperature in the range of 100° C.-130° C. for period of 5 minutes to 20 minutes to obtain a first cellulosic biomass comprising cellulose having concentration in the range of 80-95%; (ii) contacting said first cellulosic biomass with alkali having concentration in the range of 0.1-0.5% (w/w) at a temperature in the range of 100° C.-130° C. for period of 5 minutes to 30 minutes to obtain a second cellulosic biomass comprising cellulose having concentration in the range of 95-98%; and (iii) contacting said second cellulosic biomass with acid having concentration in the range of 1-3% (w/w) at a temperature in the range of 100° C.-130° C. for period of 5 minutes to 30 minutes to obtain a treated cellulosic biomass residue comprising cellulose having concentration in the range of 98-99%, (b) contacting said treated cellulosic biomass residue with cellulase having concentration of 40-50 mg/g of cellulosic biomass residue at a temperature in the range of 40° C.-50° C. for period of 90 minutes to 120 minutes to obtain a cellulose hydrolysate, and insoluble components, wherein said cellulose hydrolysate comprises sugars containing 90-98% of monomeric glucose; (c) separating the cellulose hydrolysate from cellulase and insoluble components; (d) subjecting the cellulose hydrolysate to a filtration process to obtain a permeate fraction comprising sugars, wherein said sugars comprise greater than 99% glucose, and a retentate fraction comprising oligomers, cellobiose cellotriose, and combinations thereof; (e) treating the retentate fraction with β-glucosidase to obtain a sugar solution, wherein said sugar comprises greater than 99% glucose, and separating the sugar solution from β-glucosidase; and (f) mixing the permeate fraction and sugar solution and evaporating the sugar solution to obtain greater than 98% glucose.

In an aspect of the present disclosure, there is provided a process for preparation of fructose from glucose using glucose isomerase, wherein said glucose is prepared by a method comprising the steps of: (a) subjecting a pre-treated cellulosic biomass comprising 50% to 95% cellulose to a treatment method to obtain a treated cellulosic biomass residue comprising polysaccharides containing greater than 99.0% glucose; (b) contacting said treated cellulosic biomass residue obtained from step (a) with cellulase to obtain a cellulose hydrolysate, and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The terms "pretreated cellulosic biomass" used herein refer to a cellulose composition obtained by any pretreatment of a lignocellulosic biomass such as to produce a cellulose biomass residue that is 50 to 95% cellulose.

The term "cellulosic biomass residue" used herein refers to process intermediate cellulose derived by multiple pre-treatment methods, wherein the saccharide component in the cellulose residue has 98-99.5% glucose units.

The term "high purity glucose" used herein refers to glucose obtained after enzymatic treatment with greater than 98% purity and less than 2% of other sugars.

The term "insoluble component" used herein refers to mixture of untreated cellulose and insoluble cellulase that remains after cellulase treatment.

The term "purity" or "pure" are used interchangeably and refers to assay purity which is the HPLC quantitative determination of the percentage amount of the desired component (monomeric glucose) in the dissolved sugars solids in the assayed sample (permeate and retentate fraction of cellulose hydrolysate).

The term "sugar solution" used herein refers to a solution of sugar, wherein the sugar moieties are glucose, cellobiose and other soluble oligosaccharides.

The term "cellulase" used herein refers to a category of enzymes capable of hydrolyzing cellulose (β-1,4-glucan or β-D-glucosidic linkages) to shorter oligosaccharides, cellobiose and/or glucose.

The term "β-glucosidase" used herein means a β-D-glucoside glucohydrolases that catalyze the hydrolysis of glucose oligomers, including but not limited to cellobiose, resulting predominantly in the release of corresponding sugar monomer i.e. glucose.

The term "cellulose hydrolysate" comprises oligosaccharides (cellotriose, cellotetrose etc.), disaccharides (cellobiose) and monosaccharide (glucose) units.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure as described herein.

In an embodiment of the present disclosure, there is provided a process for production of glucose having purity of greater than 98% from pre-treated cellulosic biomass comprising the steps of: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, and cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

In an embodiment of the present disclosure, there is provided a process for production of glucose having purity of greater than 98% from pre-treated cellulosic biomass as described herein, wherein glucose purity is greater than 99%.

In an embodiment of the present disclosure, there is provided a process for production of glucose having purity of greater than 98% from pre-treated cellulosic biomass as described herein, wherein said treatment method in step (a) is selected from the group consisting of acid, alkali, organosolv, ammonia fibre explosion (AFEX), ozonolysis, wet oxidation, biological methods, microwave irradiation, and combinations thereof.

In an embodiment of the present disclosure, there is provided a process for production of glucose having purity of greater than 98% from pre-treated cellulosic biomass as described herein, wherein said acid is selected from the group consisting of sulfuric acid, hydrochloric acid, hydrobromic acid, nitric acid, phosphoric acid, citric acid, oxalic acid, formic acid, acetic acid, benzoic acid, and combinations thereof, and acid concentration is in the range of 0.1% to 25% (w/w).

In an embodiment of the present disclosure, there is provided a process for production of glucose having purity of greater than 98% from pre-treated cellulosic biomass as described herein, wherein said acid concentration is in the range of 0.5% to 8% (w/w).

In an embodiment of the present disclosure, there is provided a process for production of glucose having purity of greater than 98% from pre-treated cellulosic biomass as described herein, wherein said alkali is selected from the group consisting of sodium hydroxide, potassium hydroxide, calcium hydroxide, ammonium hydroxide, ammonia, alkali derivatives, and combinations thereof, and alkali concentration is in the range of 0.1% to 25% (w/w).

In an embodiment of the present disclosure, there is provided a process for production of glucose having purity of greater than 98% from pre-treated cellulosic biomass as described herein, wherein said alkali concentration is in the range of 0.1% to 2% (w/w).

In an embodiment of the present disclosure, there is provided a process for production of glucose having purity of greater than 98% from pre-treated cellulosic biomass as described herein, wherein said treatment method is acid-acid treatment.

In an embodiment of the present disclosure, there is provided a process for production of glucose having purity of greater than 98% from pre-treated cellulosic biomass as described herein, wherein said treatment method is acid-alkali-acid treatment.

In an embodiment of the present disclosure, there is provided a process for the production of glucose having purity greater than 98%, wherein pre-treated cellulosic biomass can be converted to treated cellulosic biomass residue by acid-acid treatment method and/or acid-alkali-acid treatment method as described herein, wherein both the treatment methods provide the same amount of cellulose purity in treated cellulosic biomass residue.

In an embodiment of the present disclosure, there is provided a process for production of glucose having purity of greater than 98% from pre-treated cellulosic biomass as described herein, wherein said acid-acid treatment comprises: (a) contacting pre-treated cellulosic biomass with acid having concentration in the range of 0.5% to 8% (w/w) at a temperature in the range of 50° C. to 150° C. and for period of 5 minutes to 100 minutes to obtain a first cellulosic biomass comprising 80-95% cellulose, and (b) contacting said first cellulosic biomass with acid having concentration in the range of 0.5% to 8% (w/w) at a temperature in the range of 50° C. to 150° C. for period of 5 minutes to 100 minutes to obtain a treated cellulosic biomass residue comprising 98-99% cellulose.

In an embodiment of the present disclosure, there is provided a process for production of glucose having purity of greater than 98% from pre-treated cellulosic biomass as described herein, wherein said acid-alkali-acid treatment comprises: (a) contacting pre-treated cellulosic biomass with acid having concentration in the range of 0.5% to 8% (w/w) at a temperature in the range of 50° C. to 150° C. for period of 5 minutes to 100 minutes to obtain a first cellulosic biomass comprising 80-95% cellulose; (b) contacting the first cellulosic biomass with alkali having concentration in the range of 0.1% to 2% (w/w) at a temperature in the range of 50° C. to 150° C. for period of 5 minutes to 100 minutes to obtain a second cellulosic biomass comprising 95-98% cellulose; and (c) contacting the second cellulosic biomass with acid concentration in the range of 0.5% to 8% (w/w) at a temperature in the range of 50° C. to 150° C. for period of 5 minutes to 100 minutes to obtain a treated cellulosic biomass residue comprising 98-99% cellulose.

In an embodiment of the present disclosure, there is provided a process for production of glucose having purity of greater than 98% from pre-treated cellulosic biomass as described herein, wherein said treated cellulosic biomass residue is contacted with cellulase at a temperature in the range of 40° C. to 60° C., for period in the range of 30 minutes to 180 minutes.

In an embodiment of the present disclosure, there is provided a process for production of glucose having purity of greater than 98% from pre-treated cellulosic biomass as described herein, wherein said treated cellulosic biomass residue is contacted with cellulase at a temperature of 50° C. for a period of 120 minutes.

In an embodiment of the present disclosure, there is provided a process for production of glucose having purity of greater than 98% from pre-treated cellulosic biomass as described herein, wherein said cellulase concentration is in the range of 40 to 60 mg/g of treated cellulosic biomass.

In an embodiment of the present disclosure, there is provided a process for production of glucose having purity of greater than 98% from pre-treated cellulosic biomass as described herein, wherein said cellulase concentration is 50 mg/g of treated cellulosic biomass.

In an embodiment of the present disclosure, there is provided a process of production of glucose having purity greater than 98% wherein, cellulase may be an immobilized enzyme.

In an embodiment of the present disclosure, there is provided a process of production of glucose having purity greater than 98% wherein, production of cellulose hydrolysate may be carried out using immobilized enzyme.

In an embodiment of the present disclosure, there is provided a process of production of glucose having purity greater than 98% wherein, the immobilized systems provided work in either a reactor or packed column system.

In an embodiment of the present disclosure, there is provided an enzyme catalysed packed bed column is provided for enzymatic treatment in the presence of high concentrations of glucose or cellobiose.

In an embodiment of the present disclosure, there is provided a process for production of glucose having purity of greater than 98% from pre-treated cellulosic biomass as described herein, wherein said cellulose hydrolysate is separated by a conventional method selected from the group consisting of membrane filtration, rotary filtration, plate filtration, and combinations thereof.

In an embodiment of the present disclosure, there is provided a process for production of glucose having purity of greater than 98% from pre-treated cellulosic biomass as described herein, wherein said cellulose hydrolysate is separated by membrane filtration method.

In an embodiment of the present disclosure, there is provided a process for production of glucose having purity of greater than 98% from pre-treated cellulosic biomass as described herein, wherein filtration is carried out using a membrane having molecular weight cut off in the range of 0.1-0.3 kDa.

In an embodiment of the present disclosure, there is provided a process for production of glucose having purity of greater than 98% from pre-treated cellulosic biomass as described herein, wherein filtration is carried out using nanofiltration.

In an embodiment of the present disclosure, there is provided a process for production of glucose having purity of greater than 98% from pre-treated cellulosic biomass as described herein, wherein said sugars comprise oligosaccharides, said oligosaccharides comprising disaccharides, trisaccharides, tetrasaccharides, and combinations thereof.

In an embodiment of the present disclosure, there is provided a process for production of glucose having purity of greater than 98% from pre-treated cellulosic biomass as described herein, wherein said retentate fraction is treated with β-glucosidase at a temperature in the range of 40° C. to 60° C. and for period of 45 minutes to 60 minutes.

In an embodiment of the present disclosure, there is provided a process for production of glucose having purity of greater than 98% from pre-treated cellulosic biomass as described herein, wherein said retentate fraction is treated with β-glucosidase at a temperature of 55° C. for a period of 55 minutes.

In an embodiment of the present disclosure, there is provided a process for production of glucose having purity of greater than 98% from pre-treated cellulosic biomass as described herein, wherein β-glucosidase concentration is in the range of 10 to 85 CBU/g cellulose.

In an embodiment of the present disclosure, there is provided a process for production of glucose having purity of greater than 98% from pre-treated cellulosic biomass as described herein, wherein β-glucosidase concentration is in the range of 10 to 60 CBU/g cellulose.

In an embodiment of the present disclosure, there is provided a process of production of glucose having purity greater than 98% wherein, β-glucosidase may be an immobilized enzyme.

In an embodiment of the present disclosure, there is provided an immobilized system in which the activity of immobilized β-glucosidase is retained even after fifteen repeated cycles.

In an embodiment of the present disclosure can provide decreased residence time (about 180 minutes) for production of glucose with high purity in each reactor compared to the several hours required for in the processes disclosed in the prior arts.

The reduction of glucose adsorption and complete conversion of cellulose hydrolysate to glucose is obtained by passing the reaction mixture through the first packed bed column in upward direction and then through second packed bed column in downward direction for the residence time in the range of 15 minutes to 75 minutes at the flow rate in the range of 1.8 to 3.8 ml/minutes.

In an embodiment of the present disclosure, there is provided an immobilized enzyme system, wherein the immobilized enzyme system may be repeatedly used to treat cellulose hydrolysate for up to 15 cycles with retained activity in the range of 90 to 100%.

In an embodiment of the present disclosure, there is provided a process for separation of sugar solution from β-glucosidase by use of immobilized reactors or conventional separation methods of membrane filtration, rotary filtration, and plate filtration.

In an embodiment of the present disclosure, there is provided a process for production of glucose having purity of greater than 98% from pre-treated cellulosic biomass comprising the steps of (a) subjecting a pre-treated cellulosic biomass comprising 60% to 90% cellulose to a two-step acid-acid treatment method to obtain a treated cellulosic biomass residue comprising 98-99% cellulose, wherein said acid-acid treatment comprises: (i) contacting pre-treated cellulosic biomass with acid having concentration in the range of 1-3% (w/w) at a temperature in the range of 100° C.-130° C. for period of 5 minutes to 20 minutes to obtain a first cellulosic biomass comprising cellulose having concentration in the range of 80-95% and (ii) contacting said first cellulosic biomass with acid having concentration in the range of 1-3% (w/w) at a temperature in the range of 100° C.-130° C. for period of 5 minutes to 20 minutes to obtain a treated cellulosic biomass residue comprising cellulose having concentration in the range of 98-99%; (b) contacting said treated cellulosic biomass residue with cellulase at a concentration in the range of 40-50 mg/g of treated cellulosic biomass residue at a temperature in the range of 40° C.-50° C. for period of 90 minutes to 120 minutes to obtain cellulose hydrolysate, and insoluble components, wherein said cellulose hydrolysate comprises sugars containing 90 to 98% of monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise more than 99% glucose, and a retentate fraction comprising oligomers, cellobiose, cellotriose, and combinations thereof; (e) treating the retentate fraction with β-glucosidase to obtain a sugar solution wherein the said sugar comprises greater than 99% glucose purity, and separating the sugar solution from β-glucosidase; and (f) mixing the permeate fraction and sugar solution to obtain greater than 98% glucose purity.

In an embodiment of the present disclosure, there is provided a process for production of glucose having purity of greater than 98% from pre-treated cellulosic biomass comprising steps of: (a) subjecting pre-treated cellulosic biomass comprising 60% to 90% cellulose to a three-step acid-alkali-acid treatment method to obtain a treated cellulosic biomass residue comprising 98-99% cellulose, wherein said acid-alkali-acid treatment comprises: (i) contacting pre-treated cellulosic biomass with acid having concentration of in the range of 1-3% (w/w) at a temperature in the range of 100° C.-130° C. for period of 5 minutes to 15 minutes to obtain a first cellulosic biomass comprising cellulose having concentration in the range of 80-95%; (ii) contacting said first cellulosic biomass with alkali having concentration in the range of 0.1-0.5% (w/w) at a temperature in the range of 100° C.-130° C. for period of 5 minutes to 30 minutes to obtain a second cellulosic biomass comprising cellulose having concentration in the range of 95-98%; and (iii) contacting said second cellulosic biomass with acid having concentration in the range of 1-3% (w/w) at a temperature in the range of 100° C.-130° C. for period of 5 minutes to 30 minutes to obtain a treated cellulosic biomass residue comprising cellulose having concentration in the range of 98-99%, (b) contacting said treated cellulosic biomass residue with cellulase having concentration in the range of 40-50 mg/g of cellulosic biomass residue at a temperature in the range of 40° C.-50° C. for period of 90 minutes to 120 minutes to obtain a cellulose hydrolysate, and insoluble components, wherein said cellulose hydrolysate comprises sugars containing 90-98% of monomeric glucose; (c) separating the cellulose hydrolysate from cellulase and insoluble components; (d) subjecting the cellulose hydrolysate to a filtration process to obtain a permeate fraction comprising sugars, wherein said sugars comprise greater than 99% glucose, and a retentate fraction comprising oligomers, cellobiose cellotriose, and combinations thereof; (e) treating the retentate fraction with β-glucosidase to obtain a sugar solution, wherein said sugar comprises greater than 99% glucose, and separating the sugar solution from β-glucosidase; and (f) mixing the permeate fraction and sugar solution and evaporating the sugar solution to obtain greater than 98% glucose.

In an embodiment of the present disclosure, there is provided a process for production of glucose having purity of greater than 98% from pre-treated cellulosic biomass as described herein, wherein membrane separation of enzymes is carried out for their adequate recycling.

In an embodiment of the present disclosure, there is provided a process for production of glucose having purity greater than 98% involving an enzyme catalysed process for solubilization of the treated cellulosic biomass residue comprising polysaccharides containing greater than 98% glucose to generate cellulose hydrolysate which comprises of 90 to 98% of sugar as monomeric glucose and remaining oligosaccharides such as cellobiose and cellotriose. Subsequently, this cellulose hydrolysate is treated with β-glucosidase.

In an embodiment of the present disclosure, there is provided a process for preparation of fructose from glucose using glucose isomerase, wherein said glucose is prepared by a method as described herein.

In an embodiment of the present disclosure, there is provided glucose produced by a method as described herein, wherein said method comprises (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

In an embodiment of the present disclosure, there is provided glucose produced by a method as described herein, wherein said method comprises (a) subjecting a pre-treated cellulosic biomass comprising 60% to 90% cellulose to a two-step acid-acid treatment method to obtain a treated cellulosic biomass residue comprising 98-99% cellulose, wherein said acid-acid treatment comprises: (i) contacting pre-treated cellulosic biomass with acid having concentration in the range of 1-3% (w/w) at a temperature in the range of 100° C.-130° C. for period of 5 minutes to 20 minutes to obtain a first cellulosic biomass comprising cellulose having concentration in the range of 80-95% and (ii) contacting said first cellulosic biomass with acid having concentration in the range of 1-3% (w/w) at a temperature in the range of 100° C.-130° C. for period of 5 minutes to 20 minutes to obtain a treated cellulosic biomass residue comprising cellulose having concentration in the range of 98-99%; (b) contacting said treated cellulosic biomass residue with cellulase at a concentration in the range of 40-50 mg/g of treated cellulosic biomass residue at a temperature in the range of 40° C.-50° C. for period of 90 minutes to 120 minutes to obtain cellulose hydrolysate, and insoluble components, wherein said cellulose hydrolysate comprises sugars containing 90 to 98% of monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise more than 99% glucose, and a retentate fraction comprising oligomers, cellobiose, cellotriose, and combinations thereof; (e) treating the retentate fraction with β-glucosidase to obtain a sugar solution wherein the said sugar comprises greater than 99% glucose purity, and separating the sugar solution from β-glucosidase; and (f) mixing the permeate fraction and sugar solution to obtain greater than 98% glucose purity.

In an embodiment of the present disclosure, there is provided glucose produced by a method as described herein, wherein said method comprises: (a) subjecting pre-treated cellulosic biomass comprising 60% to 90% cellulose to a three-step acid-alkali-acid treatment method to obtain a treated cellulosic biomass residue comprising 98-99% cellulose, wherein said acid-alkali-acid treatment comprises: (i) contacting pre-treated cellulosic biomass with acid having concentration of in the range of 1-3% (w/w) at a temperature in the range of 100° C.-130° C. for period of 5 minutes to 15 minutes to obtain a first cellulosic biomass comprising cellulose having concentration in the range of 80-95%; (ii) contacting said first cellulosic biomass with alkali having concentration in the range of 0.1-0.5% (w/w) at a temperature in the range of 100° C.-130° C. for period of 5 minutes to 30 minutes to obtain a second cellulosic biomass comprising cellulose having concentration in the range of 95-98%; and (iii) contacting said second cellulosic biomass with acid having concentration in the range of 1-3% (w/w) at a temperature in the range of 100° C.-130° C. for period of 5 minutes to 30 minutes to obtain a treated cellulosic biomass residue comprising cellulose having concentration in the range of 98-99%, (b) contacting said treated cellulosic biomass residue with cellulase having concentration in the range of 40-50 mg/g of cellulosic biomass residue at a temperature in the range of 40° C.-50° C. for period of 90 minutes to 120 minutes to obtain a cellulose hydrolysate, and insoluble components, wherein said cellulose hydrolysate comprises sugars containing 90-98% of monomeric glucose; (c) separating the cellulose hydrolysate from cellulase and insoluble components; (d) subjecting the cellulose hydrolysate to a filtration process to obtain a permeate fraction comprising sugars, wherein said sugars comprise greater than 99% glucose, and a retentate fraction comprising oligomers, cellobiose cellotriose, and combinations thereof; (e) treating the retentate fraction with β-glucosidase to obtain a sugar solution, wherein said sugar comprises greater than 99% glucose, and separating the sugar solution from β-glucosidase; and (f) mixing the permeate fraction and sugar solution and evaporating the sugar solution to obtain greater than 98% glucose.

In an embodiment of the present disclosure, there is provided fructose prepared from glucose using glucose isomerase, said glucose is produced by a method as described herein.

In an embodiment of the present disclosure, there is provided fructose prepared from glucose using glucose isomerase, said glucose is produced by a method comprising: (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, and cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity.

In an embodiment of the present disclosure, there is provided fructose prepared from glucose using glucose isomerase, said glucose is produced by a method comprising: (a) subjecting a pre-treated cellulosic biomass comprising 60% to 90% cellulose to a two-step acid-acid treatment method to obtain a treated cellulosic biomass residue comprising 98-99% cellulose, wherein said acid-acid treatment comprises: (i) contacting pre-treated cellulosic biomass with acid having concentration in the range of 1-3% (w/w) at a temperature in the range of 100° C.-130° C. for period of 5 minutes to 15 minutes to obtain a first cellulosic biomass comprising cellulose having concentration in the range of 80-95% and (ii) contacting said first cellulosic biomass with acid having concentration in the range of 1-3% (w/w) at a temperature in the range of 100° C.-130° C. for period of 5 minutes to 15 minutes to obtain a treated cellulosic biomass residue comprising cellulose having concentration in the range of 98-99%; (b) contacting said treated cellulosic biomass residue with cellulase at a concentration in the range of 40-50 mg/g of treated cellulosic biomass residue at a temperature in the range of 40° C.-50° C. for period of 90 minutes to 120 minutes to obtain cellulose hydrolysate, and insoluble components, wherein said cellulose hydrolysate comprises sugars containing 90 to 98% of monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise more than 99% glucose, and a retentate fraction comprising oligomers, cellobiose, cellotriose, and combinations thereof; (e) treating the retentate fraction with β-glucosidase to obtain a sugar solution wherein the said sugar comprises greater than 99% glucose purity, and separating the sugar solution from β-glucosidase; and (f) mixing the permeate fraction and sugar solution to obtain greater than 98% glucose purity.

In an embodiment of the present disclosure, there is provided fructose prepared from glucose using glucose isomerase, said glucose is produced by a method comprising: (a) subjecting pre-treated cellulosic biomass comprising 60% to 90% cellulose to a three-step acid-alkali-acid treatment method to obtain a treated cellulosic biomass residue comprising 98-99% cellulose, wherein said acid-alkali-acid treatment comprises: (i) contacting pre-treated cellulosic biomass with acid having concentration of in the range of 1-3% (w/w) at a temperature in the range of 100° C.-130° C.

for period of 5 minutes to 15 minutes to obtain a first cellulosic biomass comprising cellulose having concentration in the range of 80-95%; (ii) contacting said first cellulosic biomass with alkali having concentration in the range of 0.1-0.5% (w/w) at a temperature in the range of 100° C.-130° C. for period of 5 minutes to 30 minutes to obtain a second cellulosic biomass comprising cellulose having concentration in the range of 95-98%; and (iii) contacting said second cellulosic biomass with acid having concentration in the range of 1-3% (w/w) at a temperature in the range of 100° C.-130° C. for period of 5 minutes to 30 minutes to obtain a treated cellulosic biomass residue comprising cellulose having concentration in the range of 98-99%, (b) contacting said treated cellulosic biomass residue with cellulase having concentration in the range of 40-50 mg/g of cellulosic biomass residue at a temperature in the range of 40° C.-50° C. for period of 90 minutes to 120 minutes to obtain a cellulose hydrolysate, and insoluble components, wherein said cellulose hydrolysate comprises sugars containing 90-98% of monomeric glucose; (c) separating the cellulose hydrolysate from cellulase and insoluble components; (d) subjecting the cellulose hydrolysate to a filtration process to obtain a permeate fraction comprising sugars, wherein said sugars comprise greater than 99% glucose, and a retentate fraction comprising oligomers, cellobiose, cellotriose, and combinations thereof; (e) treating the retentate fraction with β-glucosidase to obtain a sugar solution, wherein said sugar comprises greater than 99% glucose, and separating the sugar solution from β-glucosidase; and (f) mixing the permeate fraction and sugar solution and evaporating the sugar solution to obtain greater than 98% glucose.

In an embodiment of the present disclosure, there is provided a mixture of glucose and fructose, wherein glucose is obtained by a method as described herein, and is converted to fructose using glucose isomerase.

In an embodiment of the present disclosure, there is provided a mixture of glucose and fructose, wherein glucose is obtained by a method comprising (a) subjecting a pre-treated cellulosic biomass comprising 50% to 95% cellulose to a treatment method to obtain a treated cellulosic biomass residue comprising polysaccharides containing greater than 99.5% glucose; (b) contacting said treated cellulosic biomass residue obtained from step (a) with cellulase to obtain a cellulose hydrolysate and insoluble components, wherein said cellulose hydrolysate comprises sugars containing 90 to 98% monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise greater than 99% glucose, and a retentate fraction comprising oligomers, cellobiose, and cellotriose, and combinations thereof; (e) treating the retentate fraction with β-glucosidase to obtain a sugar solution, wherein the said sugar comprises greater than 99% glucose, and separating the sugar solution from β-glucosidase; and (f) mixing the permeate fraction and sugar solution to obtain greater than 98% glucose purity, and is converted to fructose using glucose isomerase.

In an embodiment of the present disclosure, there is provided a mixture of glucose and fructose, wherein glucose is obtained by a method comprising comprising the steps of (a) subjecting a pre-treated cellulosic biomass comprising 60% to 90% cellulose to a two-step acid-acid treatment method to obtain a treated cellulosic biomass residue comprising 98-99% cellulose, wherein said acid-acid treatment comprises: (i) contacting pre-treated cellulosic biomass with acid having concentration in the range of 1-3% (w/w) at a temperature in the range of 100° C.-130° C. for period of 5 minutes to 20 minutes to obtain a first cellulosic biomass comprising cellulose having concentration in the range of 80-95% and (ii) contacting said first cellulosic biomass with acid having concentration in the range of 1-3% (w/w) at a temperature in the range of 100° C.-130° C. for period of 5 minutes to 20 minutes to obtain a treated cellulosic biomass residue comprising cellulose having concentration in the range of 98-99%; (b) contacting said treated cellulosic biomass residue with cellulase at a concentration in the range of 40-50 mg/g of treated cellulosic biomass residue at a temperature in the range of 40° C.-50° C. for period of 90 minutes to 120 minutes to obtain cellulose hydrolysate, and insoluble components, wherein said cellulose hydrolysate comprises sugars containing 90 to 98% of monomeric glucose; (c) separating the cellulose hydrolysate from cellulase and insoluble components; (d) subjecting the cellulose hydrolysate obtained from step (c) to a filtration process to obtain a permeate fraction comprising sugars, wherein said sugars comprise more than 99% glucose, and a retentate fraction comprising oligomers, cellobiose, cellotriose and combinations thereof; (e) treating the retentate fraction with β-glucosidase to obtain a sugar solution wherein the said sugar comprises greater than 99% glucose purity, and separating the sugar solution from β-glucosidase; and (f) mixing the permeate fraction and sugar solution to obtain greater than 98% glucose purity and is converted to fructose using glucose isomerase.

In an embodiment of the present disclosure, there is provided a mixture of glucose and fructose, wherein glucose is obtained by a method comprising (a) subjecting pre-treated cellulosic biomass comprising 60% to 90% cellulose to a three-step acid-alkali-acid treatment method to obtain a treated cellulosic biomass residue comprising 98-99% cellulose, wherein said acid-alkali-acid treatment comprises: (i) contacting pre-treated cellulosic biomass with acid having concentration of in the range of 1-3% (w/w) at a temperature in the range of 100° C.-130° C. for period of 5 minutes to 15 minutes to obtain a first cellulosic biomass comprising cellulose having concentration in the range of 80-95%; (ii) contacting said first cellulosic biomass with alkali having concentration in the range of 0.1-0.5% (w/w) at a temperature in the range of 100° C.-130° C. for period of 5 minutes to 30 minutes to obtain a second cellulosic biomass comprising cellulose having concentration in the range of 95-98%; and (iii) contacting said second cellulosic biomass with acid having concentration in the range of 1-3% (w/w) at a temperature in the range of 100° C.-130° C. for period of 5 minutes to 30 minutes to obtain a treated cellulosic biomass residue comprising cellulose having concentration in the range of 98-99%, (b) contacting said treated cellulosic biomass residue with cellulase having concentration in the range of 40-50 mg/g of cellulosic biomass residue at a temperature in the range of 40° C.-50° C. for period of 90 minutes to 120 minutes to obtain a cellulose hydrolysate, and insoluble components, wherein said cellulose hydrolysate comprises sugars containing 90-98% of monomeric glucose; (c) separating the cellulose hydrolysate from cellulase and insoluble components; (d) subjecting the cellulose hydrolysate to a filtration process to obtain a permeate fraction comprising sugars, wherein said sugars comprise greater than 99% glucose, and a retentate fraction comprising oligomers, cellobiose, cellotriose and combinations thereof; (e) treating the retentate fraction with β-glucosidase to obtain a sugar solution, wherein said sugar comprises greater than 99% glucose, and separating the sugar solution from β-glucosidase; and (f) mixing the permeate fraction and sugar solution and evaporating the sugar solution to obtain greater than 98% glucose, and is converted to fructose using glucose isomerase.

In an embodiment of the present disclosure, there is provided a process for production of glucose having purity of greater than 98% from pre-treated cellulosic biomass as described herein, wherein said treated cellulosic biomass residue can result in greater than 98% cellulose purity with complete removal of xylan with less than 5% lignin from pretreated cellulosic biomass.

In an embodiment of the present disclosure, there is provided a process for production of glucose having purity of greater than 98% from pre-treated cellulosic biomass as described herein, wherein said treated cellulosic biomass residue contains less than 1% xylan.

In an embodiment of the present disclosure, there is provided a process for production of glucose having purity of greater than 98% from pre-treated cellulosic biomass as described herein, wherein said treated cellulosic biomass residue contains than 0.1% xylan.

In an embodiment of the present disclosure, there is provided a process for production of glucose having purity of greater than 98% from pre-treated cellulosic biomass as described herein, wherein said treated cellulosic biomass residue contains no xylan.

In an embodiment of the present disclosure, there is provided a process for production of glucose having purity of greater than 98% from pre-treated cellulosic biomass as described herein, where an acid or alkali is used in the pre-treatment process, at least 50% or more of that acid or alkali is recovered from the process.

In an embodiment of the present disclosure, there is provided a process involving one or more treatment steps, for isolation of cellulose residue comprising polysaccharides that contain more than 98% glucose units, from a cellulosic biomass comprising 50% to 95% cellulose. The resulting cellulose residue is amenable to enzymatic treatment for production of more than 98% monomeric glucose.

In an embodiment of the present disclosure, there is provided a consumable product comprising glucose as described herein, fructose as described herein, or a mixture of glucose and fructose as described herein, wherein the product is selected from the group consisting of a food, a beverage, a pharmaceutical composition, a tobacco product, a nutraceutical composition, an oral hygiene composition, and a cosmetic composition.

In an embodiment of the present disclosure, there is provided a beverage wherein the beverage is selected from the group consisting of enhanced sparkling beverage, cola, lemon-lime flavoured sparkling beverage, orange flavoured sparkling beverage, grape flavoured sparkling beverage, strawberry flavoured sparkling beverage, pineapple flavoured sparkling beverage, ginger-ale, soft drink, root beer, fruit juice, fruit flavoured juice, juice drink, nectar, vegetable juice, vegetable flavoured juice, sports drink, energy drink, enhanced water drink, coconut water, tea-type drink, coffee, cocoa drink, beverage containing milk components, beverage containing a cereal extract and a smoothie.

In an embodiment of the present disclosure, there is provided beverage wherein the beverage further comprises one or more functional ingredients selected from the group consisting of saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In an embodiment of the present disclosure, there is provided a consumable product comprising glucose as described herein, fructose as described herein, or a mixture of glucose and fructose as described herein, wherein the product is selected from the group consisting of a food, a beverage, a pharmaceutical composition, a tobacco product, a nutraceutical composition, an oral hygiene composition, and a cosmetic composition and wherein the beverage is selected from the group consisting of enhanced sparkling beverage, cola, lemon-lime flavoured sparkling beverage, orange flavoured sparkling beverage, grape flavoured sparkling beverage, strawberry flavoured sparkling beverage, pineapple flavoured sparkling beverage, ginger-ale, soft drink, root beer, fruit juice, fruit flavoured juice, juice drink, nectar, vegetable juice, vegetable flavoured juice, sports drink, energy drink, enhanced water drink, coconut water, tea-type drink, coffee, cocoa drink, beverage containing milk components, beverage containing a cereal extract and a smoothie.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Two Step Acid-Acid Treatment of Pretreated Cellulosic Biomass for Production of Treated Cellulosic Biomass Residue comprising Greater than 98% Cellulose 10 g of pretreated cellulosic biomass was mixed with 190 g of 2% (w/w) nitric acid in a 400 ml high-pressure reactor. The reaction mixture was heated to 130° C. for 15 minutes and then cooled to RT (room temperature, 22-28° C.). The slurry was filtered to obtain a first cellulosic biomass comprising cellulose of 80-95% purity and a filtrate. The filtrate obtained was subjected to membrane filtration to separate hydrolyzed lignin and xylose from acid [Table 1(a)]. The first solid residue was mixed with 90 g of 2% (w/w) nitric acid in same reactor. The reaction mixture was heated to 130° C. for 15 minutes and then cooled to RT (room temperature, 22-28° C.). The slurry was filtered to obtain treated cellulosic biomass residue [Table 1(b)]. The filtrate was subjected to membrane filtration to recover acid.

TABLE 1(a)

Purity of first cellulosic biomass obtained after first acid (nitric acid) treatment

| pretreated cellulosic biomass purity (substrate for first acid treatment) | Purity of pretreated cellulosic biomass component (%) before first acid treatment | | | Purity of first cellulosic biomass component obtained after first acid treatment (%) | | |
|---|---|---|---|---|---|---|
| % | Cellulose | Xylan | Lignin | Cellulose | Xylan | Lignin |
| 60 | 60 | 25 | 15 | 80 | 8 | 12 |
| 80 | 80 | 15 | 5 | 90 | 6 | 4 |
| 90 | 90 | 8 | 2 | 95 | 4 | 1 |

TABLE 1(b)

Purity of cellulose in treated cellulosic biomass residue obtained after second acid (nitric acid) treatment

| First cellulosic biomass purity (%) (substrate for second acid treatment) | Purity of first cellulosic biomass component after first acid treatment (%) | | | Purity of treated cellulosic biomass component obtained after second acid treatment (%) | | |
|---|---|---|---|---|---|---|
| | Cellulose | Xylan | Lignin | Cellulose | Xylan | Lignin |
| 80 | 80 | 8 | 12 | 98 | Nil | 2 |
| 90 | 90 | 6 | 4 | 98.5 | Nil | 1.5 |
| 95 | 95 | 4 | 1 | 99 | Nil | 1 |

Example 1 provides purity of cellulose in treated cellulosic biomass residue obtained after acid-acid treatment, wherein Table 1(a) provides purity of cellulose in first cellulosic biomass obtained after first nitric acid treatment. It is clear from Table 1(a), that there is enrichment in the percentage of cellulose and reduction in the percentage of xylan and lignin; and Table 1(b) provides purity of cellulose in treated cellulosic biomass obtained after second nitric acid treatment. It is clear from table 1(b) that on treatment of first cellulosic biomass with nitric acid there is enrichment of cellulose percentage in treated cellulosic biomass residue with about 0% xylan and less than 1% lignin.

Example 2

Three Step Acid-Alkali-Acid Treatment for Production of a Treated Cellulosic Biomass Residue comprising Greater than 98% Cellulose 100 g of pretreated cellulosic biomass was mixed with 1900 kg of 2% (w/w) nitric acid in 5 L high-pressure reactor. The reaction mixture was heated to 130° C. for 15 minutes and then cooled to RT (room temperature, 22-28° C.) gradually. After cooling, the slurry was filtered to obtain a first cellulosic biomass comprising cellulose having 80 to 95% purity, and a filtrate. The filtrate obtained was subjected to membrane filtration to separate hydrolyzed lignin and xylan from nitric acid. The first cellulosic biomass was mixed with 900 g of 0.5% (w/w) NaOH in same reactor. The reaction mixture was heated to 120° C. for 30 minutes and then cooled to RT (room temperature, 22-28° C.) gradually. After cooling, the slurry was filtered to obtain a second cellulosic biomass comprising cellulose of 95 to 98% purity. The second cellulosic biomass was mixed with 620 g of 2% (w/w) nitric acid. The reaction mixture was heated to 120° C. for 30 minutes and then cooled to RT (room temperature, 22-28° C.) gradually. After cooling, the slurry was filtered to obtain treated cellulosic biomass residue. The filtrate was subjected to membrane filtration to recover acid.

TABLE 2(a)

Purity of first cellulosic biomass obtained after first Acid treatment

| Pretreated cellulosic biomass purity (substrate for first nitric acid treatment) | Purity of pretreated cellulosic biomass component (%) before acid treatment | | | Purity of first cellulosic biomass component obtained after first nitric acid treatment (%) | | |
|---|---|---|---|---|---|---|
| % | Cellulose | Xylan | Lignin | Cellulose | Xylan | Lignin |
| 60 | 60 | 25 | 15 | 80 | 8 | 12 |
| 80 | 80 | 15 | 5 | 90 | 6 | 4 |
| 90 | 90 | 8 | 2 | 95 | 4 | 1 |

TABLE 2(b)

Purity of second cellulosic biomass obtained after Alkali treatment

| First cellulosic biomass purity (substrate for alkali treatment) | Purity of first cellulosic biomass component (%) after first acid treatment | | | Purity of second cellulosic biomass component obtained after alkali treatment (%) | | |
|---|---|---|---|---|---|---|
| % | Cellulose | Xylan | Lignin | Cellulose | Xylan | Lignin |
| 80 | 80 | 8 | 12 | 95 | 2 | 3 |
| 90 | 90 | 6 | 4 | 97 | 0.5 | 2.5 |
| 95 | 95 | 4 | 1 | 98 | Nil | 2 |

TABLE 2(c)

Purity of treated cellulosic biomass residue obtained after Second acid treatment

| Second cellulosic biomass purity (substrate for second acid treatment) | Purity of cellulose component (%) in second cellulosic biomass after alkali treatment | | | Purity of cellulose component (%) treated cellulosic biomass residue obtained after acid treatment | | |
|---|---|---|---|---|---|---|
| % | Cellulose | Xylan | Lignin | Cellulose | Xylan | Lignin |
| 95 | 95 | 2 | 3 | 98 | Nil | 2 |
| 97 | 97 | 0.5 | 2.5 | 98.5 | Nil | 1.5 |
| 98 | 98 | Nil | 2 | 99 | Nil | 1 |

TABLE 2(d)

Effect of acid and alkali concentration on the purity of the cellulose in treated cellulosic biomass residue

| (a) Nitric acid conc. (w/w) | (b) Temp (° C.) | (c) Time (minutes) | (d) NaOH conc. (w/w) | (e) Temp (° C.) | (f) Time (minutes) | (g) Nitric acid conc. (w/w) | (i) Temp (° C.) | (j) Time (minutes) | Cellulose Purity (%) |
|---|---|---|---|---|---|---|---|---|---|
| 0.5 | 100 | 5  | 0.1 | 100 | 5  | 0.5 | 100 | 5  | 95   |
| 1   | 120 | 15 | 0.5 | 120 | 15 | 1   | 120 | 15 | 97   |
| 2   | 120 | 15 | 0.5 | 120 | 30 | 2   | 120 | 30 | 99.5 |
| 4   | 130 | 20 | 0.5 | 130 | 30 | 4   | 130 | 30 | 99   |
| 6   | 130 | 20 | 1.5 | 130 | 30 | 6   | 130 | 30 | 99   |
| 8   | 120 | 25 | 2   | 120 | 45 | 8   | 120 | 45 | 97   |

Example 2 provides purity of cellulose in treated cellulosic biomass residue obtained after acid-alkali-acid treatment, wherein Table 2(a) provides purity of cellulose in first cellulosic biomass obtained after first nitric acid treatment, Table 2(b) provides purity of cellulose in treated cellulosic biomass obtained after alkali treatment, Table 2(c) provides purity of cellulose in treated cellulosic biomass obtained after nitric acid treatment and Table 2(d) provides effect of acid and alkali concentration at varying time and temperatures on the purity of the cellulose in treated cellulosic biomass residue. It is clear from Table 2(d) that if acid-alkali-acid treatment of pre-treated cellulosic biomass is carried out to obtain treated cellulosic biomass residue then the highest cellulose purity is obtained when nitric acid concentration is 2% (w/w) at a temperature of 130° C. for a period of 15 minutes and NaOH concentration is 0.5% (w/w) at a temperature of 110° C. and for a period of 15 minutes.

Example 3

Enzymatic Hydrolysis of Treated Cellulosic Biomass Obtained after Treatment

Treated cellulosic biomass residue obtained from the two step acid-acid treatment and three step acid-alkali-acid was enzymatically hydrolysed using commercial cellulases. 1 g of cellulose residue, was suspended in 100 ml of acidified water with pH5 in a 250 ml conical flask to make 1% (w/v) slurry suspension. Cellulase was added at a protein loading of 83 mg/g of cellulose to each flask. These flasks were incubated for 12 hour in a rotary shaker maintained at 50° C. and 200 rpm. The cellulose hydrolysate obtained was passed through an ultrafiltration membrane to retain the insoluble solid residue and the cellulase. Table 3 provides % enzymatic hydrolysis of treated cellulosic biomass residue to obtain cellulose hydrolysate

TABLE 3

Cellulose conversion after enzymatic hydrolysis

| Biomass type | Biomass loading | Enzyme loading | Temperature (° C.) | % Hydrolysis |
|---|---|---|---|---|
| Treated cellulosic biomass obtained after two step acid-acid treatment | 1% | 83 mg/g | 50° C. | 92.68% |
| Treated cellulosic biomass obtained after three step acid-alkali-acid treatment | | | | 94.59% |

Example 4

Production of Purified Glucose Using Cellulose Produced in Example 1

Treated cellulosic biomass residue obtained from two step acid-acid treatment was used to obtain a high purity glucose solution. 50 g of treated cellulosic biomass residue, was suspended in 1000 ml of acidified water (pH 5) in a 1500 ml jacketed reactor connected to a membrane module to make a slurry suspension of 5% (w/v). The slurry was mixed at 200 rpm using an overhead stirrer, hot water circulation was provided to maintain the reactor at 50° C. and the pH was adjusted to 5 using 1M NaOH. Cellulase was added at a protein loading of 50 mg/g of cellulose and allowed to hydrolyse for 2 h (Table 4). The cellulose hydrolysate obtained was passed through an ultrafiltration membrane to retain the insoluble solid residue and the cellulase. The clear cellulose hydrolysate, comprising of 88.18% glucose, 10.21% cellobiose and 1.23% cellotriose was passed through a filtration membrane having molecular weight cut off in the range of 0.2-0.3 kDa to permeate glucose and retain cello-oligomers. The retentate was then treated with β-glucosidases to hydrolyse the residual cello-oligomers (Table 4). Following which it was passed through an ultrafiltration membrane to retain the enzyme and permeate glucose solution with 99.03% glucose and 0.5% cellobiose. Table 4 provides glucose purity obtained after sequential enzymatic hydrolysis.

Example 5

Production of High Purity Glucose Using Cellulose Produced in Example 2

Treated cellulosic biomass residue (98-99%) obtained from three step acid-alkali-acid treatment was used to obtain high purity glucose solution. 35 g of treated cellulose biomass residue was suspended in 700 ml of acidified water (pH5) to make a slurry suspension of 5% (w/v) in a jacketed reactor connected to a membrane module. The slurry was mixed at 200 rpm using an overhead stirrer, hot water circulation was provided to maintain the reactor at 50° C. and the pH was adjusted to 5 using 1M NaOH. Cellulase was added at a protein loading of 50 mg/g of cellulose and allowed to hydrolyse for 2 h (Table 4). The cellulose hydrolysate obtained was passed through an ultrafiltration membrane to retain the insoluble solid residue and the cellulase. The clear cellulose hydrolysate comprising of 88.70% glucose, 9.87% cellobiose and 1.15% cellotriose was passed through a filtration membrane having molecular weight cut off in the range of 0.2-0.3 kDa to permeate glucose and retain cello-oligomers. The retentate was then treated with ß-glucosidases, to hydrolyse the residual cello-oligomers (Table 4). Following which it was passed through an ultrafiltration membrane to retain the enzyme and permeate glucose solution with 99.05% glucose and 0.5% cellobiose.

TABLE 4

Glucose purity obtained after enzymatic hydrolysis

| Treated Cellulosic biomass residue (% cellulose purity) | Cellulase mg/g cellulose | Time (minutes) | Temp. (° C.) | Glucose purity (%) | β-glucosidase CBU/g | Temp. (° C.) | Time (minutes) | Glucose purity (%) |
|---|---|---|---|---|---|---|---|---|
| 98 | 30 | 120 | 50 | 79.69% | 15 | 55 | 55 | 96.81% |
| 98 | 30 | 120 | 50 | 80.44% | 45 | 55 | 55 | 97.39% |
| 98 | 50 | 120 | 50 | 88.50% | 45 | 55 | 55 | 98.75% |
| 98 | 50 | 120 | 50 | 89.01% | 60 | 55 | 55 | 99.05% |
| 98 | 50 | 120 | 50 | 88.92% | 60 | 55 | 60 | 99.07% |
| 99 | 50 | 120 | 50 | 88.18% | 15 | 55 | 55 | 96.24% |
| 99 | 80 | 120 | 50 | 92.15% | 15 | 55 | 55 | 95.72% |
| 99 | 50 | 120 | 50 | 87.95% | 45 | 55 | 45 | 97.65% |
| 99 | 50 | 120 | 50 | 88.70% | 45 | 55 | 55 | 95.84% |
| 99 | 50 | 120 | 50 | 89.14% | 45 | 55 | 60 | 98.38% |
| 99 | 50 | 60 | 50 | 82.51% | 60 | 55 | 55 | 95.61% |
| 99 | 50 | 120 | 50 | 88.76% | 60 | 55 | 55 | 99.02% |
| 99 | 50 | 180 | 50 | 90.72% | 60 | 55 | 55 | 99.03% |

Table 4 provides the purity of glucose obtained after the enzymatic hydrolysis with cellulase and β-glucosidases. It is clear from Table 4 that when treated cellulosic biomass residue is treated with cellulase, cellulose hydrolysate is obtained in the retentate fraction which comprises glucose purity in the range of 82%-92%. The permeate fraction obtained after treatment with cellulase is subjected to β-glucosidases treatment to obtain greater than 98% glucose purity.

The present disclosure provides a process for production of glucose having purity greater than 98% from pretreated cellulosic biomass comprising 50-95% cellulose, using thermal, chemical and enzymatic treatments. The process of the present disclosure involves mild acid-acid and/or acid-alkali-acid treatment of the pretreated cellulosic biomass for production of treated cellulosic biomass residue comprising polysaccharides containing greater than 98% glucose units. The treatment resulted in high purity cellulose that is highly amenable to controlled enzymatic reaction with cellulase to obtain cellulose hydrolysate and the insoluble components. Further the cellulose hydrolysate and the insoluble components were subjected to filtration process to obtain a permeate fraction and a retenate fraction. Permeate fraction comprised of sugars wherein said sugars comprised of grater than 99% glucose units in it. The retentate fraction comprised of oligomers, cellobiose and cellotriose which was further subjected to enzymatic treatment with β-glucosidase to obtain a sugar solution wherein the said sugar solution comprised of greater than 99% glucose units in it. The process of the disclosure also involves membrane separation of enzymes and oligosaccharides for recycling and separation of glucose to avoid product feedback inhibition, and yield glucose having purity greater than 98%.

The advantage of the present process showed high efficiency in terms of conversion, shorter reaction time and better utilization of enzyme and hence improved economics than known in the art.

The present disclosure provides a process for generation of cellulose hydrolysate through an enzyme catalysed process. The cellulose hydrolysate was generated using a controlled enzymatic reaction with cellulases. The enzymes, chemicals and solvents in the system can be recycled, in some cases to more than 95%, to ensure least pollution load and adequate economy of production. The present invention provides shorter reaction time with higher conversion rate (greater than 90%) resulting in increased productivities for the process over conventional processes. This technology provides rapid and continuous process steps for large scale implementation, and allows use of all types of biomass feedstocks from low-lignin soft to high-lignin hard biomass feedstocks. It is of importance to note that the conversion of cellulose hydrolysate to glucose having greater than 98% purity can be attained in time period in the range of 30 minutes to 180 minutes. The process takes care of product inhibition of the enzyme used even with the use of low β-glucosidase and enhances the conversion of the cellulose hydrolysate to glucose so as to obtain sugar solutions, wherein sugar solution contains greater than 98% glucose purity. The process can result in at least 50% recovery of acid, in the examples in which acid is used for pretreatment. In some of the embodiments, the use of mild acids at low temperatures (up to 150° C.) also reduces formation of sugar degradation products. The alkali and acid used in the process can be recycled in the process. The water used was also recycled, thus making the plant based on the present technology a potentially zero discharge facility with the lignin being recovered and no significant amounts of salts formed in any of the process steps.

We claim:

1. A process for production of glucose having purity of greater than 98% from pre-treated cellulosic biomass comprising the steps of:
    a) subjecting a pre-treated cellulosic biomass comprising 50% to 95% cellulose to a treatment method to obtain a treated cellulosic biomass residue comprising polysaccharides containing greater than 99.5% glucose moieties;
    b) contacting said treated cellulosic biomass residue obtained from step (a) with cellulose to obtain a cellulose hydrolysate, and insoluble components, wherein said cellulose hydrolysate comprises sugars containing 90 to 98% monomeric glucose;

c) separating the cellulose hydrolysate from cellulose and insoluble components;

d) subjecting the cellulose hydrolysate obtained from step (a) to a filtration process to obtain a permeate fraction comprising sugars, wherein said sugars comprise greater than 99% glucose and a retentate fraction comprising oligomers, cellobiose, and cellotriose, or combinations thereof;

e) treating the retentate fraction with β-glucosidase to obtain a sugar solution, wherein the said sugar comprises greater than 99% glucose, and separating the sugar solution from β-glucosidase; and f) mixing the permeate fraction and the sugar solution to obtain greater than 98% glucose purity.

2. The process as claimed in claim 1 wherein the glucose purity is greater than 99%.

3. The process as claimed in claim 1, wherein said treatment method in step (a) is selected from the group consisting of acid, alkali, organosolv, ammonia fibre explosion (AFEX), ozonolysis, wet oxidation, biological methods, microwave irradiation, and combinations thereof.

4. The process as claimed in claim 3, wherein said acid is selected from the group consisting of sulfuric acid, hydrochloric acid, hydrobromic acid, nitric acid, phosphoric acid, citric acid, oxalic acid, formic acid, acetic acid, benzoic acid, or combinations thereof, and acid concentration is in the range of 0.1% to 25% (w/w).

5. The process as claimed in claim 4, wherein said acid concentration is in the range of 0.5% to 8% (w/w).

6. The process as claimed in claim 3, wherein said alkali is selected from the group consisting of sodium hydroxide, potassium hydroxide, calcium hydroxide, ammonium hydroxide, ammonia, alkali derivatives, or combinations thereof, and alkali concentration is in the range of 0.1% to 25% (w/w).

7. The process as claimed in claim 6, wherein said alkali concentration is in the range of 0.1% to 2% (w/w).

8. The process as claimed in claim 3, wherein the said treatment method is selected from the group consisting of acid-acid treatment, and acid-alkali-acid treatment.

9. The process as claimed in claim 8, wherein said acid-acid treatment comprises:

a) contacting pre-treated cellulosic biomass with acid having concentration in the range of 0.5% to 8% (w/w) at a temperature in the range of 50° C. to 150° C. and for a period of 5 minutes to 100 minutes to obtain a first cellulosic biomass comprising 80% to 95% cellulose, and b) contacting said first cellulosic biomass with acid having concentration in the range of 0.5% to 8% (w/w) at a temperature in the range of 50° C. to 150° C. for period of 5 minutes to 100 minutes to obtain a treated cellulosic biomass residue comprising 98-99% cellulose.

10. The process as claimed in claim 8, wherein said acid-alkali-acid treatment comprises:

a) contacting pre-treated cellulosic biomass with acid having concentration in the range of 0.5% to 8% (w/w) at a temperature in the range of 50° C. to 150° C. for period of 5 minutes to 100 minutes to obtain a first cellulosic biomass comprising 80% to 95% cellulose;

b) contacting the first cellulosic biomass with alkali having concentration in the range of 0.1% to 2% (w/w) at a temperature in the range of 50° C. to 150° C. for period of 5 minutes to 100 minutes to obtain a second cellulosic biomass comprising 95-98% cellulose; and c) contacting the second cellulosic biomass with acid concentration in the range of 0.5% to 8% (w/w) at a temperature in the range of 50° C. to 150° C. for period of 5 minutes to 100 minutes to obtain a treated cellulosic biomass residue comprising 98-99% cellulose.

11. The process as claimed in claim 1, wherein said treated cellulosic biomass residue is contacted with cellulase at a temperature in the range of 40° C. to 60° C. for period in the range of 30 minutes to 180 minutes.

12. The process as claimed in claim 1, wherein said cellulase concentration is in the range of 40 to 60 mg/g of treated cellulosic biomass.

13. The process as claimed in claim 1, wherein said cellulose hydrolysate is separated by a conventional method selected from the group consisting of membrane filtration, rotary filtration, plate filtration, and combinations thereof.

14. The process as claimed in claim 1, wherein said sugars comprise oligosaccharides, said oligosaccharides comprising disaccharides, trisaccharides, tetrasaccharides, or combinations thereof.

15. The process as claimed in claim 1, wherein said retentate fraction is treated with β-glucosidase at a temperature in the range of 40° C. to 60° C. and for a period in the range of 45 minutes to 60 minutes.

16. The process as claimed in claim 1, wherein said β-glucosidase concentration is in the range of 10 CBU/g to 85 CBU/g of cellulose.

17. A process for production of glucose having purity of greater than 98% from pre-treated cellulosic biomass comprising the steps of:

a) subjecting a pre-treated cellulosic biomass comprising 60% to 90% cellulose to a two-step acid-acid treatment method to obtain a treated cellulosic biomass residue comprising 98-99% cellulose, wherein said acid-acid treatment comprises;

(i) contacting pre-treated cellulosic biomass with acid having concentration in the range of 1% (w/w) to 3% (w/w) at a temperature in the range of 100° C. to 130° C. for period of 5 minutes to 20 minutes to obtain a first cellulosic biomass comprising cellulose having concentration in the range of 80-95%; and (ii) contacting said first cellulosic biomass with acid having concentration in the range of 1% (w/w) to 3% (w/w) at a temperature in the range of 100° C. to 130° C. for period of 5 minutes to 20 minutes to obtain a first cellulosic biomass comprising cellulose having concentration in the range of 98-99%;

b) contacting said treated cellulosic biomass residue with cellulose at a concentration in the range of 40 mg/g to 50 mg/g of treated cellulosic biomass residue at a temperature in the range of 40° C. to 50° C. for period of 90 minutes to 120 minutes to obtain cellulose hydrolysate, and insoluble components, wherein said cellulose hydrolysate comprises sugars containing 90 to 98% of monomeric glucose;

c) separating the cellulose hydrolysate from cellulose and insoluble components;

d) subjecting the cellulose hydrolysate obtained from step (c) to a filtration process to obtain a permeate fraction comprising sugars, wherein said sugars comprise more than 99% glucose and a retentate fraction comprising oligomers, cellobiose, cello-triose or combinations thereof;

e) treating the retentate fraction with β-glucosidase to obtain a sugar solution wherein the said sugar comprises greater than 99% glucose purity, and separating the sugar solution from β-glucosidase; and f) mixing the permeate fraction and the sugar solution to obtain greater than 98% glucose purity.

18. The process as claimed in claim 1, wherein said filtration is nanofiltration.

19. A process for production of glucose having purity of greater than 98% from pre-treated cellulosic biomass comprising the steps of:
- a) subjecting pre-treated cellulosic biomass comprising 60% to 90% cellulose to a three-step acid-alkali-acid treatment method to obtain a treated cellulosic biomass residue comprising 98% to 99% cellulose, wherein said acid-alkali-acid treatment comprises:
  - (i) contacting pre-treated cellulosic biomass with acid having concentration of 1% (w/w) to 3%% (w/w) at a temperature in the range of 100° C. to 130° C. for period of 5 minutes to 1 minutes to obtain a first cellulosic biomass comprising cellulose having concentration in the range of 80% to 95%;
  - (ii) contacting said first cellulosic biomass with alkali having concentration in the range of 0.1% to −0.5% (w/w) at a temperature in the range of 100° C. to 130° C. for period of 5 minutes to 30 minutes to obtain a second cellulosic biomass comprising cellulose having concentration in the range of 95% to 98%; and
  - (iii) contacting said second cellulosic biomass with acid having concentration in the range of 1% to 3% (w/w) at a temperature in the range of 100° C. to 130° C. for period of 5 minutes to 30 minutes to obtain a treated cellulosic biomass residue comprising cellulose having concentration in the range of 98% to 99%,
- b) contacting said treated cellulosic biomass residue with cellulase having concentration in the range of 40 mg/g to 50 mg/g of cellulosic biomass residue at a temperature in the range of 40° C. to 50° C. for period of 90 minute to 120 minutes to obtain a cellulose hydrolysate, and insoluble components, wherein said cellulose hydrolysate comprises sugars containing 90-98% of monomeric glucose;
- c) separating the cellulose hydrolysate from cellulase and insoluble components;
- d) subjecting the cellulose hydrolysate to a filtration process to obtain a permeate fraction comprising sugars, wherein said sugars comprise greater than 99% glucose and a retentate fraction comprising oligomers, cellobiose, cellotriose, or combinations thereof;
- e) treating the retentate fraction with β-glucosidase to obtain a sugar solution, wherein said sugar comprises greater than 99% glucose, and separating the sugar solution from β-glucosidase; and
- f) mixing the permeate fraction and the sugar solution and evaporating the sugar solution to obtain greater than 98% glucose.

20. A process for preparation of fructose from glucose comprising preparing glucose by a method as claimed in claim 1; and converting the glucose to fructose using glucose isomerase.

21. The process as claimed in claim 19, wherein said filtration is nanofiltration.

* * * * *